US007366618B2

(12) United States Patent
McPherson et al.

(10) Patent No.: US 7,366,618 B2
(45) Date of Patent: Apr. 29, 2008

(54) DATABASE SYSTEM AND METHOD FOR ANALYZING AND ASSOCIATING OBSERVABLE DATA WITH SUBSTANCES, EQUIPMENT, AND PROCESSES

(75) Inventors: Devin McPherson, Arlington, VA (US); Deborah Lynn Althoff, Arlington, VA (US); Scott Lilienthal, Laurel, MD (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/315,098

(22) Filed: Dec. 23, 2005

(65) Prior Publication Data

US 2007/0150209 A1    Jun. 28, 2007

(51) Int. Cl.
*G01N 19/00* (2006.01)
(52) U.S. Cl. .......................................... 702/30; 706/46
(58) Field of Classification Search ................ 702/30, 702/183, 22; 707/104.1
See application file for complete search history.

(56) References Cited

U.S. PATENT DOCUMENTS

| 6,885,975 | B2* | 4/2005 | Srinivasan et al. ......... 702/183 |
| 6,937,939 | B1* | 8/2005 | Shibusawa et al. .......... 702/22 |
| 2004/0003000 | A1* | 1/2004 | Smith et al. .............. 707/104.1 |
| 2005/0118637 | A9* | 6/2005 | Levinson et al. ............ 435/7.1 |
| 2006/0010090 | A1* | 1/2006 | Brockway et al. ........... 706/46 |

OTHER PUBLICATIONS

ChemReact 68, DVD Edition, by Cambridge Soft, retrieved from the internet on Dec. 7, 2005.
ChemSynth CD-Rom Edition, by Cambridge Soft, retrieved from the internet on Dec. 7, 2005.
Advanced Recipe Search Feature, by Epicurious, retrieved from the internet on Dec. 7, 2005.

* cited by examiner

*Primary Examiner*—John E. Barlow, Jr.
*Assistant Examiner*—Xiuqin Sun
(74) *Attorney, Agent, or Firm*—Edell, Shapiro & Finnan, LLC

(57) ABSTRACT

A database system and method are provided to allow a user to characterize observations related to an otherwise unidentified process. A database is established that stores data for substances, processes and equipment according to a data model that relates attributes of substances, processes and equipment. Information related to observations, called observed data or observables, is entered by a user into the system as the search criteria. The observed data may range in complexity from the names of one or more substances and/or processing equipment to a text description of the odor, color and state of observed substances and/or equipment. The system searches the database using the search criteria to return a list of one or more processes that possibly create the observed data, and thus more completely characterize the process.

35 Claims, 23 Drawing Sheets

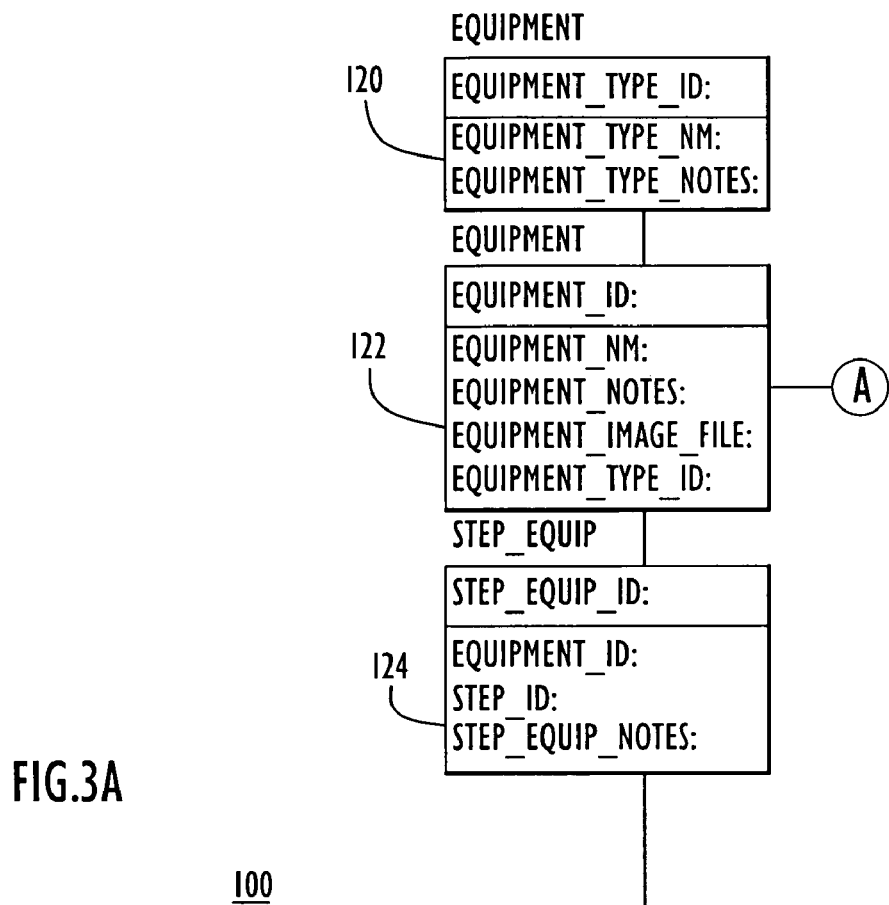
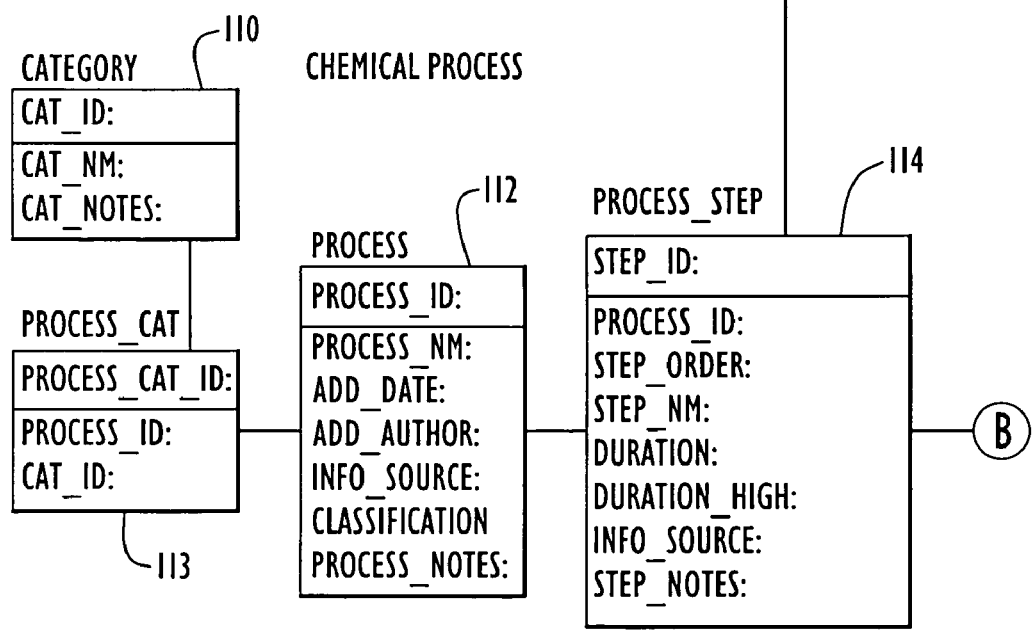
FIG.3A

FIG.6B

CHEMICAL

Chemical Process Database

Processes — 412
Chemicals — 412
Equipment — 414

410

Search For: brown solid — 424

Filter By: Chemical Category ▼  Chemical Comments ▼ Filter — 422

| "Pyro" Compound | |
|---|---|
| [((2-Chloroethylthio)Ethyl)((2-Chloroethoxy)Ethyl)]Ether | Add To Search |
| [((2-Hydroxyethylthio)Ethyl)((2-Chloroethylthio)Ethyl)]Ether | Add To Search |
| [((2-Hydroxyethylthio)Ethyl)((2-Mercaptoethoxy)Ethyl)]Ether | Add To Search |
| [((2-Hydroxyethylthio)Ethyl)]Vinyl Ether | Add To Search |
| [((Vinylsulfonyl)Ether)((Vinylthio)Ethyl)]Ether | Add To Search |
| [((Vinylsulfonyl)Ethyl)((Vinylsulfinyl)Ethyl)]Ether | Add To Search |
| (2-Chloroethyl)(2-Hydroxyethyl)Ether | Add To Search |
| (2-Chloroethylsulfinyl)(2-Chloroethylthio)Ethane | Add To Search |
| (2-Chloroethylsulfonyl)(2-Chloroethyl)Vinyl Ether | Add To Search |
| (2-Chloroethylsulfonyl)(2-Chloroethylsulfinyl)Ethane | Add To Search |
| (2-Chloroethylsulfonyl)(2-Chloroethylthio)Ethane | |

Figure 7:
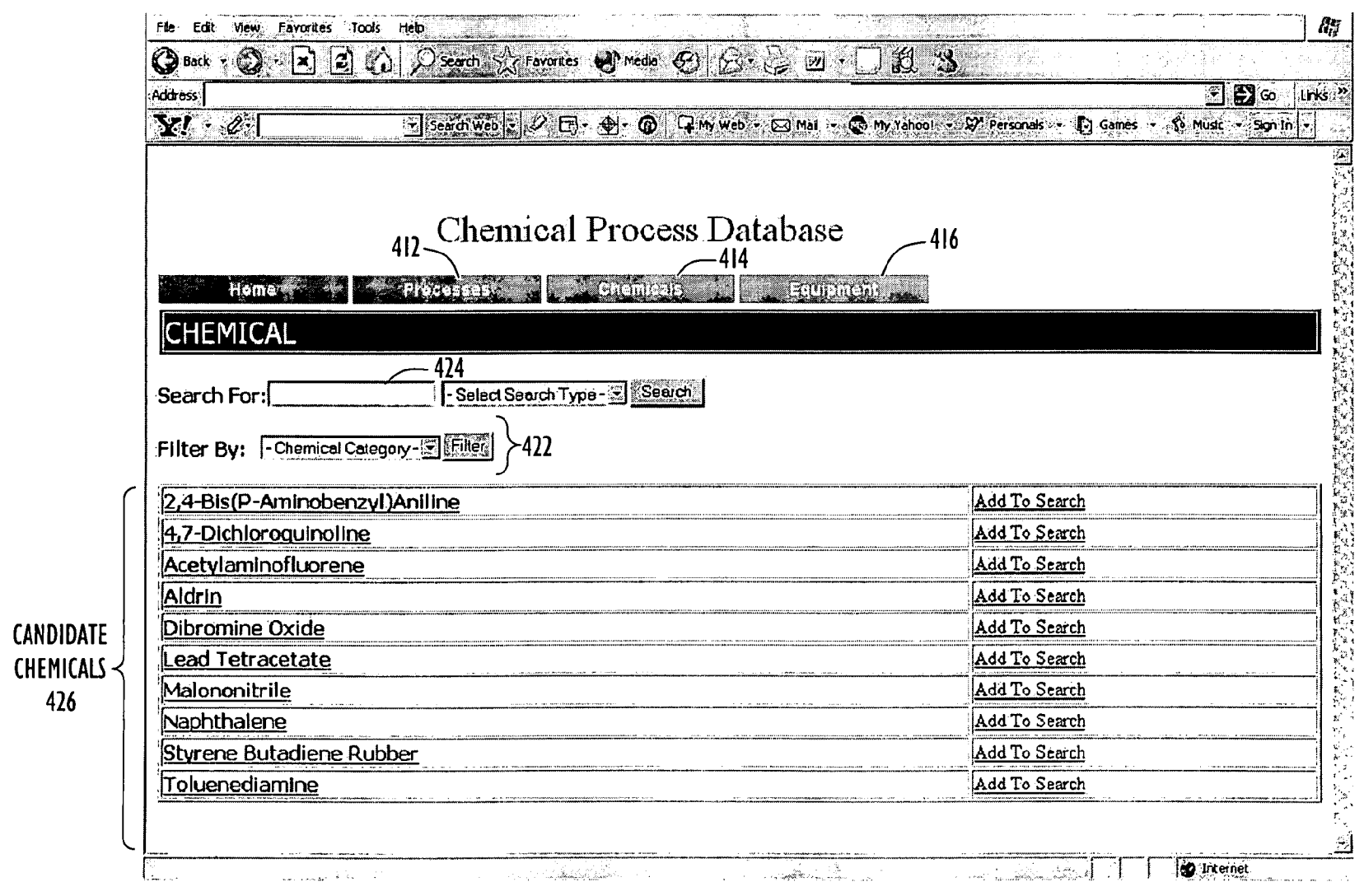

Chemical Process Database

CHEMICAL

Search For: [_____] -Select Search Type- [Search]

Filter By: [-Chemical Category-] [Filter]

| | |
|---|---|
| 2,4-Bis(P-Aminobenzyl)Aniline | Add To Search |
| 4,7-Dichloroquinoline | Add To Search |
| Acetylaminofluorene | Add To Search |
| Aldrin | Add To Search |
| Dibromine Oxide | Add To Search |
| Lead Tetracetate | Add To Search |
| Malononitrile | Add To Search |
| Naphthalene | Add To Search |
| Styrene Butadiene Rubber | Add To Search |
| Toluenediamine | Add To Search |

CANDIDATE CHEMICALS 426

Observables for: Methylenedianiline Process 1

| Chemical Name | CAS | Formula | State | Use |
|---|---|---|---|---|
| 2,4-Bis(4-Aminobenzyl)Aniline | 25834-80-4 | H2NC6H4CH2C6H3(CH2C6H4NH2)NH2 | - | Product |
| 4,4-Methylenedianiline | 101-77-9 | C13H14N2 | - | Reactant |
| Aniline | 62-53-3 | C6H5NH2 | - | Reactant |
| Anilinium Ion | | C6H5NH3+ | - | Reactant |
| Ethanesulfonic Acid | 594-45-6 | C2H6O3S | - | Reactant |
| Formaldehyde | 50-00-0 | CH2O | - | Reactant |
| Hydrogen Chloride | 7647-01-0 | HCl | - | Reactant |
| Hydrogen Ion | | H+ | - | Reactant |
| Methylene Diphenyl Diisocyanate | 12408-02-5 | C15H10N2O2 | - | Product |
| N,N'-Aminobenzyl-Aniline | 101-68-8 | C13H14N2 | - | Reactant |
| N-Metholaniline | 17272-83-2 | C7H9NO | - | Reactant |
| P-Aminobenzyl Carbonium Ion | 61274-12-6 | NH2C6H4CH2+ | - | Reactant |
| Phosgene | 75-44-5 | CCl2O | - | Reactant |
| Quinazoline | 253-82-7 | C8H6N2 | - | Emmission |
| Silicon Dioxide | 7631-86-9 | SiO2 | - | Reactant |
| Sodium Hydroxide | 1310-73-2 | NaOH | - | Reactant |
| Tungsten | 7440-33-7 | W | - | Reactant |
| Water | 7732-18-5 | H2O | - | Product |

FIG. 15

Chemical Process Database

EQUIPMENT

Search For: [          ]

Filter By: [-Equipment Type-] [Filter]

| | |
|---|---|
| Combustion - Basic Oxygen Furnace | Add To Search |
| Combustion - Binary burners | Add To Search |
| Combustion - Blast furnace | Add To Search |
| Combustion - Brick-lined Furnace | Add To Search |
| Combustion - Carbon Tube Furnace | Add To Search |
| Combustion - Cast Iron Retort | Add To Search |
| Combustion - Catalytic Cracker | Add To Search |
| Combustion - Combustion Chamber | Add To Search |
| Combustion - Continuous Furnace | Add To Search |
| Combustion - Drum Type Furnace | Add To Search |
| Combustion - Electrical Induction Furnace | Add To Search |
| Combustion - Electrical Oven | Add To Search |
| Combustion - Flash Tower | Add To Search |

| | CAS | Chemical Name |
|---|---|---|
| Emmission | 74-84-0 | Ethane |
| Emmission | 111-46-6 | Diethylene Glycol |
| Emmission | 1344-28-1 | Aluminum Oxide |
| Emmission | 7631-86-9 | Silicon Dioxide |
| Emmission | 68-12-2 | Dimethylformamide |
| Emmission | 872-50-4 | 1-Methyl-2-Pyrrolidinone |

Step Name: 5 - Propene Finishing

Step Duration:

Step Notes: Similarly, after separation the C3 fraction, the propyne and allene present must be converted (by selective hydrogenation) into propene or propane before the propene/propane separation. Propene can be recovered in about 99.9 % purity.

Equipment Used:

| | CAS | Chemical Name | Qty | Volume Unit | State |
|---|---|---|---|---|---|
| | | Separate: | | | |
| Reactant | 74-99-7 | Propyne | | | |
| Reactant | 463-49-0 | Allene | | | |
| Product | 115-07-1 | Propene | | | |
| Product | 74-98-6 | Propane | | | |
| Emmission | 74-99-7 | Propyne | | | |
| Emmission | 463-49-0 | Allene | | | |
| Emmission | 115-07-1 | Propene | | | |
| Emmission | 74-98-6 | Propane | | | |

View Printable Format

View Process Observables

FIG.20

Observables for: Ethylene and Propene from Naptha Cracking

| Chemical Name | CAS | Formula | State | Use |
|---|---|---|---|---|
| 1-Methyl-2-Pyrrolidinone | 872-50-4 | CH3NCH2CH2CH2CO | | Reactant |
| Acetylene | 74-86-2 | C2H2 | | Reactant |
| Allene | 463-49-0 | C3H4 | | Reactant |
| Aluminum Oxide | 1344-28-1 | Al2O3 | | Reactant |
| C4 Fraction | | C4Hx | | Reactant |
| C5 Fraction | | C5Hx | | Reactant |
| Carbon Dioxide | 124-38-9 | CO2 | | Emmission |
| Chromium | 7440-47-3 | Cr | | Reactant |
| Diethylene Glycol | 111-46-6 | O(C2H4OH)2 | | Reactant |
| Dimethylformamide | 68-12-2 | HCON(CH3)2 | | Reactant |
| Ethane | 74-84-0 | C2H6 | | Reactant |
| Ethylene | 74-85-1 | C2H4 | | Reactant |
| Hydrogen | 1333-74-0 | H2 | | Reactant |
| Hydrogen Sulfide | 7783-06-4 | H2S | | Emmission |
| Methane | 74-82-8 | CH4 | | Reactant |
| Naphtha/Gasoline | 8006-61-9 | | | Reactant |
| Nickel | 7440-02-0 | Ni | | Product |
| Propane | 74-98-6 | C3H8 | | Reactant |
| Propene | 115-07-1 | C3H6 | | Reactant |
| Propyne | 74-99-7 | CH3CHC | | Reactant |
| Silicon Dioxide | 7631-86-9 | SiO2 | | Reactant |

DATABASE SYSTEM AND METHOD FOR ANALYZING AND ASSOCIATING OBSERVABLE DATA WITH SUBSTANCES, EQUIPMENT, AND PROCESSES

BACKGROUND OF THE INVENTION

1. Field of the Invention

The present invention is directed to a software tool to assist investigators with analysis of data relating to various activities and phenonomenologies, in particular, in associating observable data with related chemical substances, equipment, and processes.

2. Description of the Related Art

Man-made substances are generally produced by performing a series of processing steps in which substances are contacted in a particular manner and sequence, to generate a desired final product. There are needs to link resources to activities for purposes of evaluating capabilities or forensically deducing activities from piecemeal information. Given a finite set of resources, an example of an evaluation of capabilities is in the development of a meal plan. An inventory of foodstuffs can be used in a range of recipes to generate a number of dishes. A means of assessing the potential alternatives could be used by a restaurant for optimizing inventory exploitation. This approach could be used in the chemical process industry as well. An example of using certain information forensically to infer potential activities involves nonproliferation analysis for weapons of mass destruction. In a typical scenario, an investigator may be interested in understanding the capabilities of a suspected facility to produce banned chemical weapons agents instead of advertised products. This investigator may infer various scenarios given different legitimate and illegitimate activities that may be occurring at the suspect site. To ascertain the capabilities of the facility, the investigator would have to use a highly trained chemical engineer and or a library of technical support information to determine the chemicals, equipment, and processing steps required to produce various illicit chemical agents or alternative, advertised products. If the analyst has certain information about the facility, it may also be possible to deduce the nature of the activities. The available information would have to be integrated with the detailed chemical engineering domain knowledge much the same as the above inferencing process.

For the inference, the information or "observables" may be in the form of chemical by-products present in the soil, water, or air, observable features of a processing facility (e.g., a smoke stack of a certain size), discovery of specific equipment, etc. Such scenarios are increasingly common, for example, in the field of non-proliferation and data gathering, where it is important to monitor the activity of chemical facilities and suspicious sites for illegal, dangerous chemicals. However, very often it is impossible to directly monitor the facilities to obtain sufficient information.

It is recognized that there is no replacement for a knowledgeable expert or a technical library, but it is possible to harness essential information to support the activities of this expert. Conventional resources such as textbooks, other literature, and existing databases are often distributed and decentralized, and they do not facilitate investigation of alternatives given a variety of constraints. It is desired to have a single source as a convenient, comprehensive tool for the investigation of observable clues to discover what activities or capabilities might be associated with them. There is no product known that facilitates this kind of activity.

SUMMARY OF THE INVENTION

Briefly, a database system and method are provided to allow a user to characterize observables related to an otherwise unidentified activity. A database is established that stores data for substances, processes and equipment according to a data model that relates observable data to data for substances, processes and equipment. Observable data is data that can be detected or discovered in connection with a particular chemical, process or equipment. A process is a set of human activities for manufacture or production typically involving multiple steps. Examples of processes are chemical processes, biological processes, nuclear processes. Information related to observations, called observed data, is entered by a user into the system as search criteria. The observed data may range in complexity from the names of one or more substances and/or processing equipment to a text description of the odor, color and state of observed substances and/or equipment. The system searches the database using the search criteria to return a list of one or more processes that possibly create the observed data, and thus more completely characterize the process.

The system displays detailed information about each process, including each step, piece of equipment and substance involved in the process. Furthermore, the system also displays a list that includes other observable data associated with the process. These additional observables may include substances, equipment and other information that is observable through visual or other detection means. A user may use the list of observables to conduct further investigation in order to better characterize of the process(es) occurring.

BRIEF DESCRIPTION OF THE DRAWINGS

FIGS. 3A, 3B and 3C are diagrams depicting a data model useful for the system and methods according to the present invention.

FIG. 6B illustrates the chemical search screen of the system, and entry of observed data for the search criteria according to a first search example.

FIGS. 7-11 are subsequent user interface screen displays associated with the first search example.

FIGS. 12-20 are user interface screen displays associated with a second search example.

DETAILED DESCRIPTION

Figure 1:
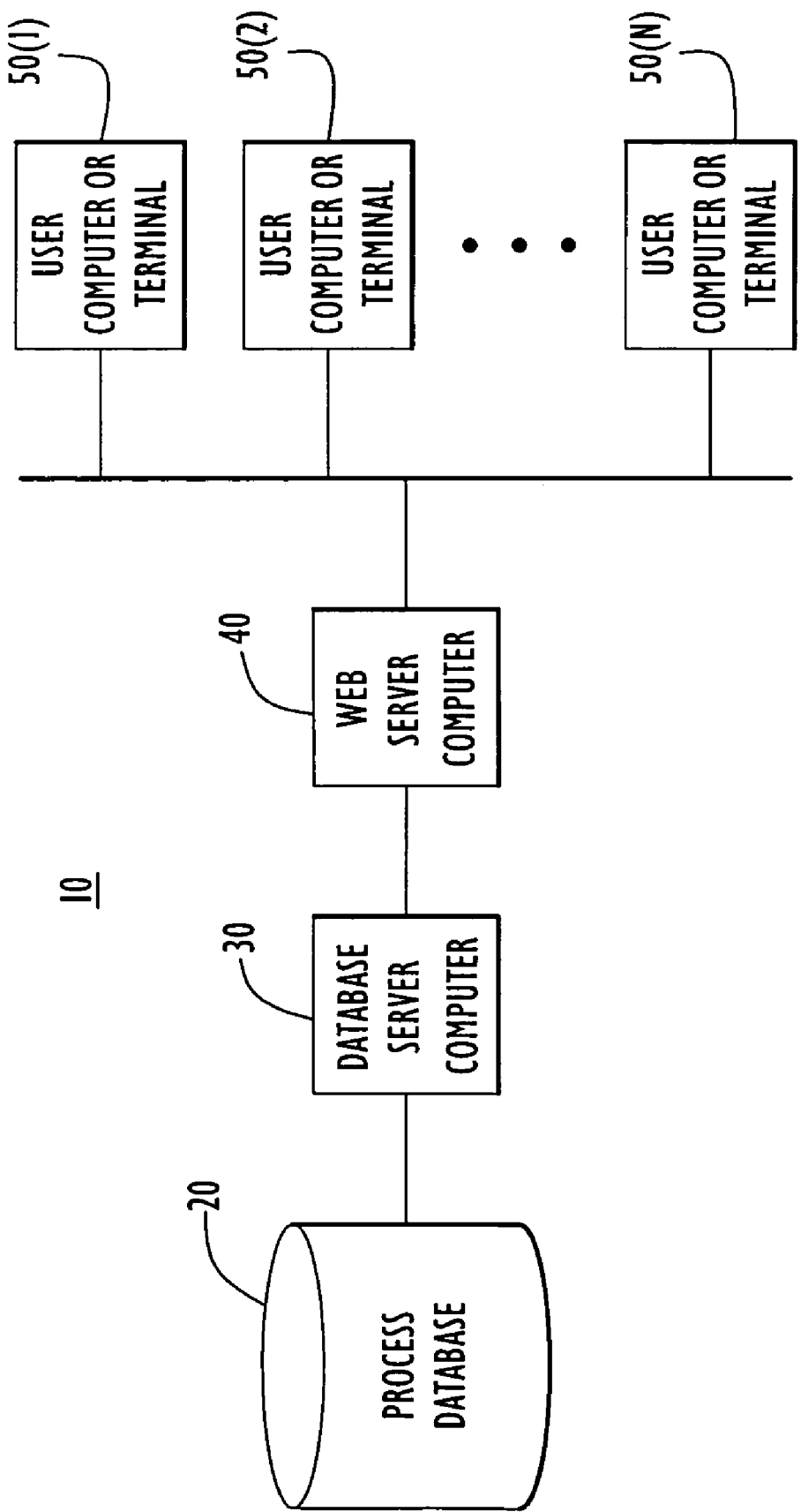
FIG. 1 is a general block diagram of the database system according to the present invention.

Referring first to FIG. 1, a characterization database system is shown at reference numeral 10 comprising a process database 20, a database server computer 30 and a web server computer 40. The database 20 is embodied by a suitable data storage device and access to and from the data is managed by the database server computer 30 running a database software application. For example, the database 20 and database server computer 30 may be part of a database system. User access to the system may be from one or more local or remote user terminals 50(1) to 50(N). For example, the user terminals may be computers that connect to the web server 40 via one or more data networks (e.g., the internet and/or an intranet) collectively represented at reference numeral 60. Alternatively, it should be understood that the system 10 may be implemented in a stand-alone form comprising the database 20, server computer 30 and one user computer or terminal.

The database 20 may be designed to support counterproliferation activities in the analysis of suspect illicit chemical weapons production processes. For example, the production processes included in the database may include processes for manufacturing or processing chemical weapons, biological weapons, nuclear weapons and explosives. However, the database 20 may also store data for commercial processes. The database 20 allows the user to characterize observations made from afar or in other inconspicuous ways using various information observing or gathering techniques. This knowledge or information is referred to hereinafter as "observed data".

Figure 2:
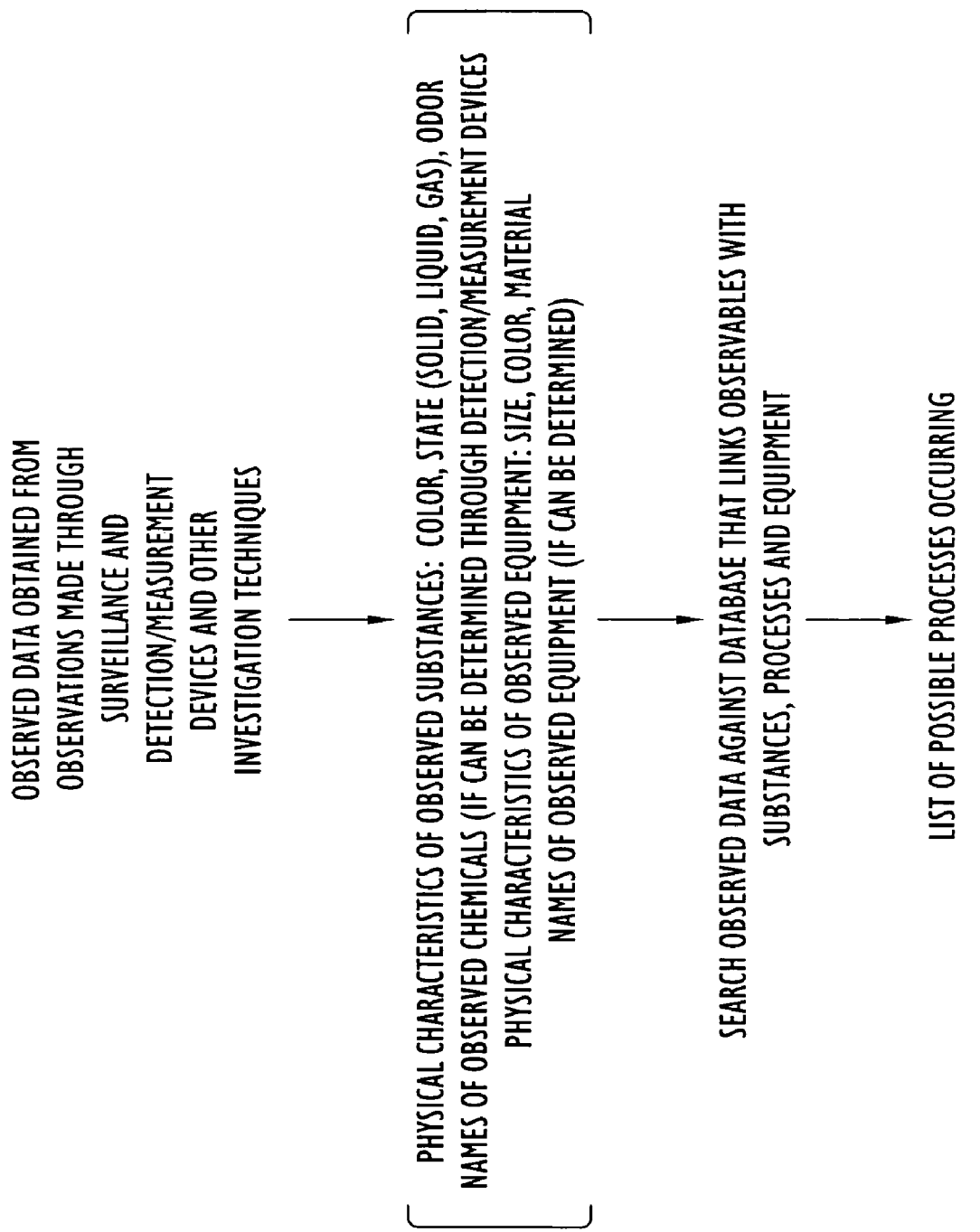
FIG. 2 is a general data flow diagram for the chemical process characterization methods according to the present invention.

Turning to FIG. 2, one application scenario of the system 10 will be described. Suppose an unusual chemical substance is observed, such as one that may be related to the illegal production of dangerous substances, such as chemical, biological or nuclear weapons or materials for such weapons. The observed data are collected through a variety of remote (and perhaps undetectable) observation or detection/measurements. Examples of observed data include physical characteristics of observed substances, names of the observed substances, physical characteristics of the observed equipment, and names of the observed equipment. Physical characteristics of observed substances may be descriptions of the color, (red, brown, yellow, etc.), state of the substance (solid, liquid, gas), odor, etc. If it is possible to positively identify the substance by chemical name through one or more chemical identification equipment, then the observed data would include the chemical name (and other characteristics determined with such equipment) of each observed substance, in addition to, or instead of, its observed physical characteristics. Similarly, physical characteristics of the observed equipment may include size, color, material, etc., of the structures observed at a facility, such as cooling tower, furnace, smoke stack, materials for those physical structures (bricks, steel, etc.)

Next, a user supplies the observed data into the database to search for all potentially matching or related chemicals, processes and/or equipment. The database links or relates data for observables with data for chemicals, processes and equipment. The system returns a list of possible (candidate) chemical processes occurring. The list of candidate chemical processes may be further analyzed to guide a user to make other observations that would be useful to narrow down the list of candidate processes to the most likely one (or ones).

Figure 3B:
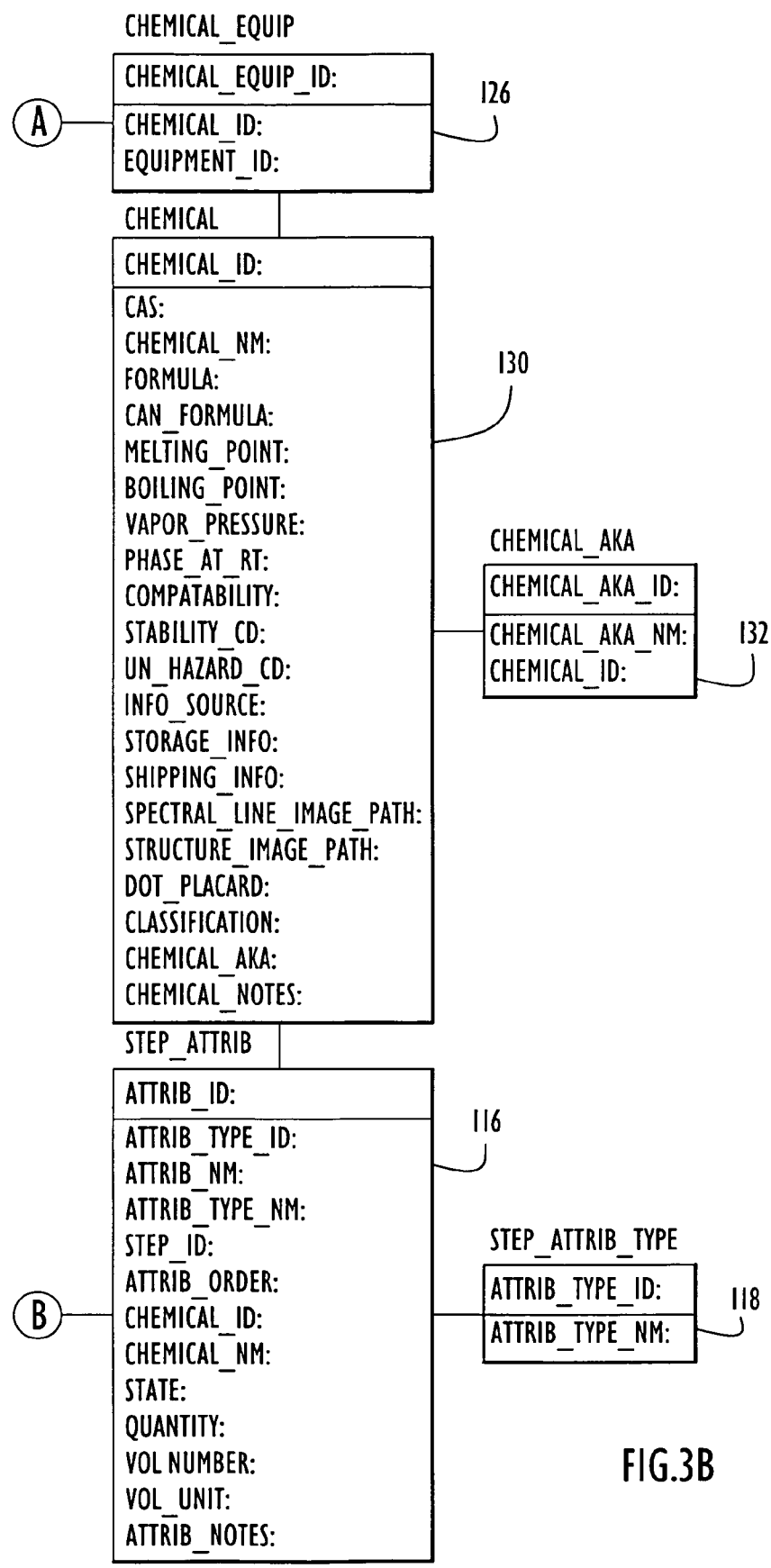
Figure 3C:
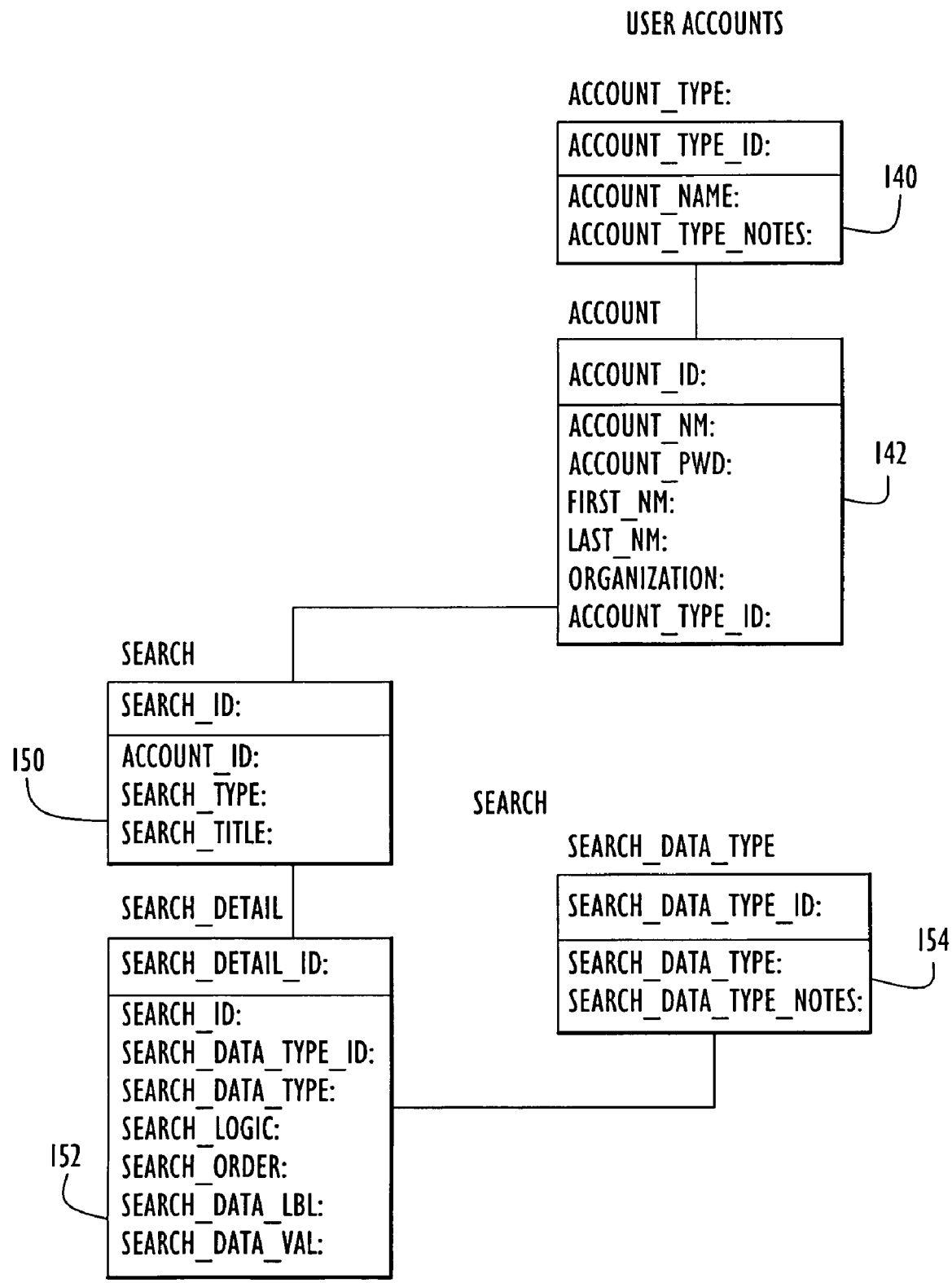

Turning to FIGS. 3A, 3B and 3C, a data model 100 useful for the chemical process database as search criteria will be described. The data model 100 is based on a relational database that links records based on categories and other searchable characteristics. More specifically, the database maintains associations or relationships between chemicals, processes and equipment (and other types of data) to allow a user to enter a set of observables and return a set of candidate processes that may be occurring that create those observables.

The database comprises interrelated data elements or records pertaining to a plurality chemicals, a plurality of processes and a plurality of chemical processing equipment. There are records for chemical category (Category) 110, Process 112, Process Category 113, Process Step 114, Step Attribute 116 and a Step Attribute Type (step_attrib_type) 118. With respect to equipment, there are records for Equipment Type 120, Equipment 122, Equipment Step (step_equip) 124 and Chemical Equipment (chemical_equip) 126. For each chemical in the database, there is a Chemical Identifier (chemical_id) 130 record and a chemical "also known as" (AKA) or "other names" record 132. There are also records for user accounts including an Account Type 140 and an Account 142. Finally, there are records associated with search data, including Search 150, Search Detail 152 and a Search Data Type 154. These records have multiple fields, certain ones of which are interrelated as explained below.

| Category Record 110 | |
|---|---|
| Cat_ID | Number that is used to identify a category, typically an integer. |
| Cat_NM | Name of the category. (Name is abbreviated "NM".) |
| Cat_Notes | Brief text-based description of the category |

Examples of chemical categories are alcohols, acid chlorides, ketones, sulfides, thiols, oximes, etc.

| Process Record 112 | |
|---|---|
| Process_ID | Number that is used to identify a process, typically an integer. |
| Process_NM | Name of the Process. |
| Add_Date | Date that this data was added to the database. |
| Add_Author | Name of the person or "author" that added this data to the database. |
| Info_Source | The source of the information for this data record, e.g., reference book or other publication. |
| Classification | Indication whether the data is "Classified" and can be viewed only by individuals with a certain security clearance, or "Unclassified". |
| Process_Notes | Brief text-based description of the process. |

Examples of process categories are agrochemicals, adhesives, chemical weapons, biological, ceramics, chemical industry, explosives, food & beverage, etc. A process and chemical can be in more than one category.

| Process Category Record 113 | |
|---|---|
| Process_Cat_ID | Number that is used to identify a process category, typically an integer. |
| Process_ID | Identifier of the process. |
| Cat_ID | Chemical category identifier. |

Note that a Category record 110 is related to a Process Category record by the Cat_ID data.

| Process Step 114 | |
|---|---|
| Step_ID | Number that is used to identify a category. Typically an integer. |
| Process_ID | Number that is used to identify a process step. |
| Step_Order | The order that the step occurs among a sequence of steps. |
| Step_NM | Name of the step. |
| Duration | Time duration of the step. |
| Duration_High | Maximum time duration of the step. |
| Info_Source | The Source used for the information in this data record. |
| Cat_Notes | Brief text-based description of the category |

A process is comprised of one or more process steps, and each step is given a Step ID in the database. A step may occur in a particular sequence in the overall process, and thus, the Step Order data specifies this. Process ID, from the Process record 112, is also a field in the Process Category record 113 and in the Process Step record 114.

| Step Attribute (Step_Attrib) 116 | |
|---|---|
| Attrib_ID | Number to identify a step attribute. |
| Attrib_Type_ID | Number to identify a "type" assigned to the step attribute. |
| Attrib_NM | Name for the Step Attribute. |
| Attrib_Type_NM | Name for the "type" of step attribute. |
| Step_ID | Identifier of a related process step record 114. |
| Attrib_Order | The order in which the data is displayed. |
| Chemical_ID | Identifier or a related chemical for the step attribute. |
| Chemical NM | Name of the related chemical for the Step Attribute. |
| State | The physical state (gas, liquid or solid) of the chemical(s) in the Step Attribute. |
| Quantity | Number indicating a quantity amount. |
| Vol_Number | Number indicating a volume amount. |
| Vol_Unit | Volume units. |
| Attrib_Notes | Text description pertaining to the step attribute. |

| Step Attribute Type (Step_Attrib_Type) 118 | |
|---|---|
| Attrib_Type_ID | Number that is used to identify the attribute type, typically an integer. |
| Attrib_Type NM | Name of the attribute type. |

| Equipment_Type 120 | |
|---|---|
| Equipment_Type_ID | Number that is used to identify an equipment type, typically an integer. |
| Equipment_Type_NM | Name of the equipment type. |
| Equipment_Type_Notes | Brief text-based description of the equipment type |

| Equipment 122 | |
|---|---|
| Equipment_ID | Number to identify the equipment. |
| Equipment_NM | Name of the equipment. |
| Equipment_Notes | Brief textual description of the equipment. |
| Equipment_Image_File | Image file of the equipment (e.g., JPG, BMP, TIFF, etc.) |
| Equipment_Type_ID | Number of the corresponding equipment Type. |

| Step_Equip 124 | |
|---|---|
| Step_Equip_ID | Number to identify the equipment. |
| Equipment_ID | Name of the equipment. |
| Step_ID | Brief textual description of the equipment. |
| Step_Equip_Notes | Image file of the equipment (e.g., JPG, BMP, TIFF, etc.) |

| Chemical_Equip 126 | |
|---|---|
| Chemical_Equip_ID | Number to identify the chemical equipment. |
| Chemical_ID | Identifier of each of the related chemical(s) pertaining to this Chemical_Equip_ID. |
| Equipment_ID | Identifier of the related equipment. |

The Chemical Equipment data record describes equipment associated with chemical handling and storage, whereas Process Equipment is equipment associated with processing.

| Chemical 130 | |
|---|---|
| Chemical_ID | Number to identify the Chemical. |
| CAS | The official CAS assigned to the Chemical |
| Chemical_NM | Name for the Chemical. |
| Formula | Formula for the Chemical. |
| Can_Formula | Canonical formula for the Chemical. |
| Storage-Info | Information pertaining to how the Chemical is safely stored. |
| Shipping_Info | Information pertaining to how the Chemical is shipped. |
| Classification | Indication whether the data is "Classified" and can be viewed only by individuals with a certain security clearance, or "Unclassified". |
| Chemical-AKA | Other commonly used names for the Chemical. |
| Chemical Notes | Text description about the chemical, its dangers and uses. |

Those fields shown in FIGS. 3A, 3B and 3C for that Chemical record 130 that have a meaning obvious to one with ordinary skill are omitted from the table for simplicity.

| Chemical AKA 132 | |
|---|---|
| Chemical_AKA_ID | Number to identify the Chemical AKA. |
| Chemical_AKA_NM | Name of the Chemical AKA, i.e., other name commonly used for the Chemical. |
| Chemical_ID | Identifier of the related Chemical to which the chemical_AKA pertains. |

The Account Type record 140 comprises an account type ID, and for each account type ID, there are fields for account name and account type notes. The Account record 142 comprises an account ID, and for each account ID there are fields for account NM, account password, first name, last name, organization and account type ID.

The Search record 150 comprises a search ID, and for each search ID there are fields for account ID, search type and search title. The Search Detail record 152 comprises a search detail ID, and for each search detail ID, there are fields for search ID, search data type ID, search data type, search logic, search order, search data label and search data value. The Search Data Type record 154 comprises a search data type ID, and for each search type ID there are fields for search data type and search data type notes.

When building the database, data for a chemical may be gathered and entered as follows. The processes of making that chemical are researched. For each process, the chemicals, steps and equipment needed for the various process steps are determined. Information is included for each of the chemicals in the process, and the role of the chemical, e.g., catalyst, solvent, reactant, product, byproduct, emission, etc. For each step of a process, the actions that occur are determined. These actions correspond to the types of equipment needed to carry out those actions in the process.

Figure 4:
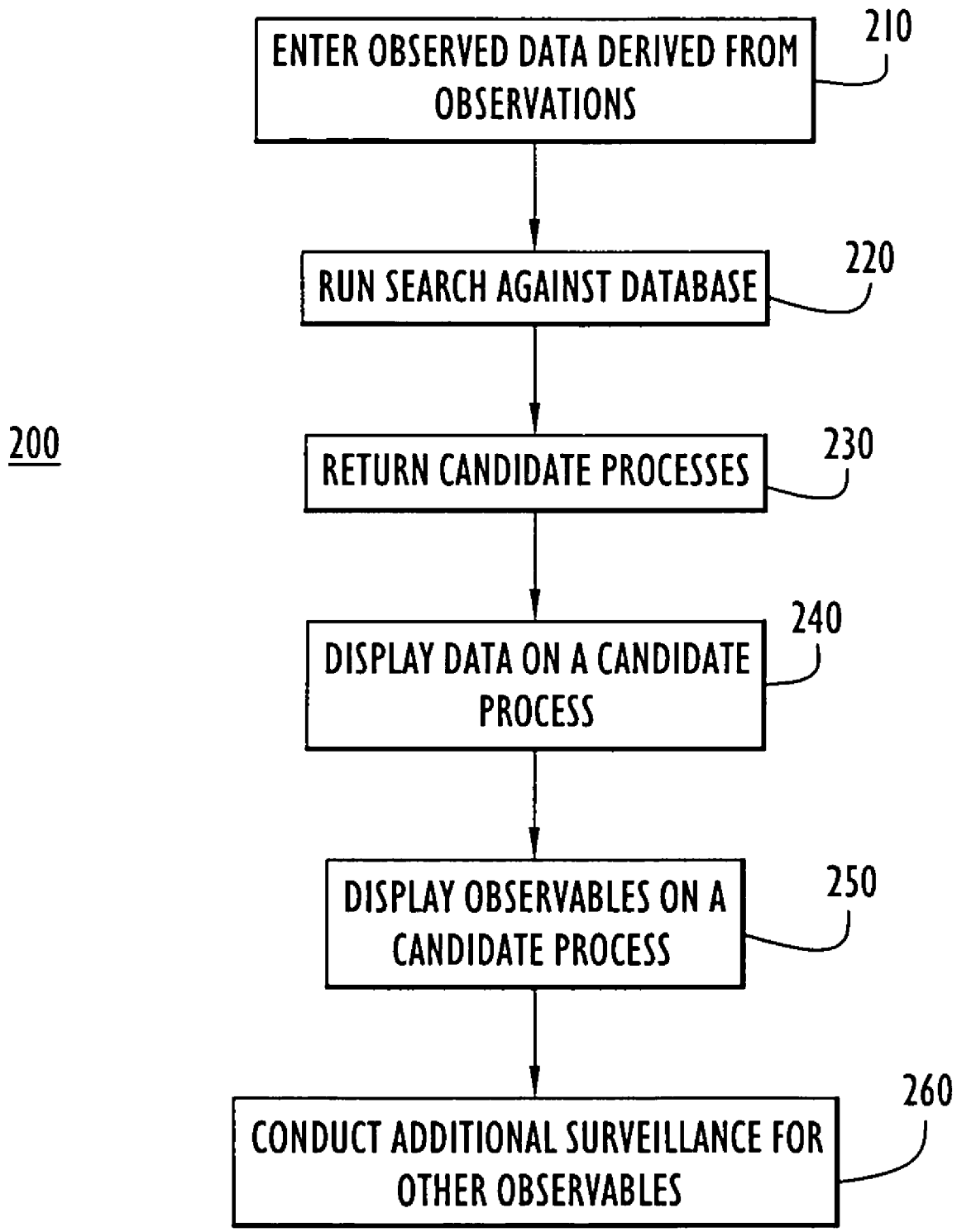
FIG. 4 is a general flow chart for the chemical process characterization method according to the present invention.

Turning now to FIG. 4, a description is provided of a chemical process characterization method 200 using a database such as the one shown in FIG. 3 and described above. In step 210, a user enters observed data (associated with the observables), obtained through one or more surveillance or investigation measures described above. In step 220, a search is executed against the database using the observed data as search terms. In step 230, the search may be a multi-tiered SQL search against the data in the database to return all candidate chemical processes that are possibly occurring based on the observed data. Bayesian analysis may be performed during the search to provide an indication of a percentage of match likelihood for each of the search results. Next, in step 240, data is displayed for the list of zero or more candidate chemical processes that match the observed data entered in to step 210. A user may examine details for each candidate process, such as a list of the steps in the process, as well as a list of observables for that process. In step 260, the user may study the list of observables for one or more candidate processes in order to conduct additional investigation to see if those additional observables are present, providing further indication of a likely match with a particular candidate process.

Figure 5:
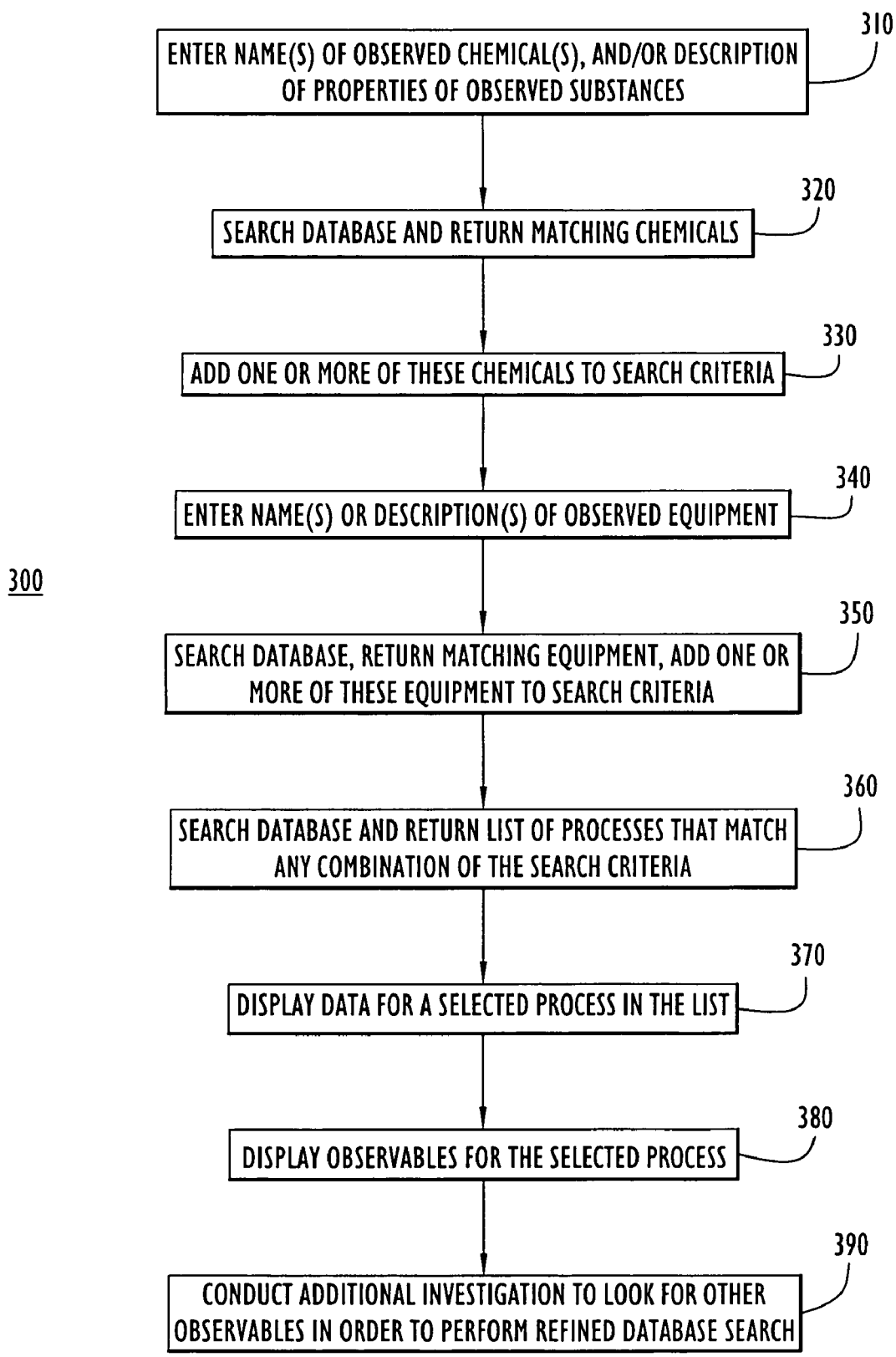
FIG. 5 is a more detailed flow chart for embodiments of the chemical characterization method according to the present invention.
Figure 6A:
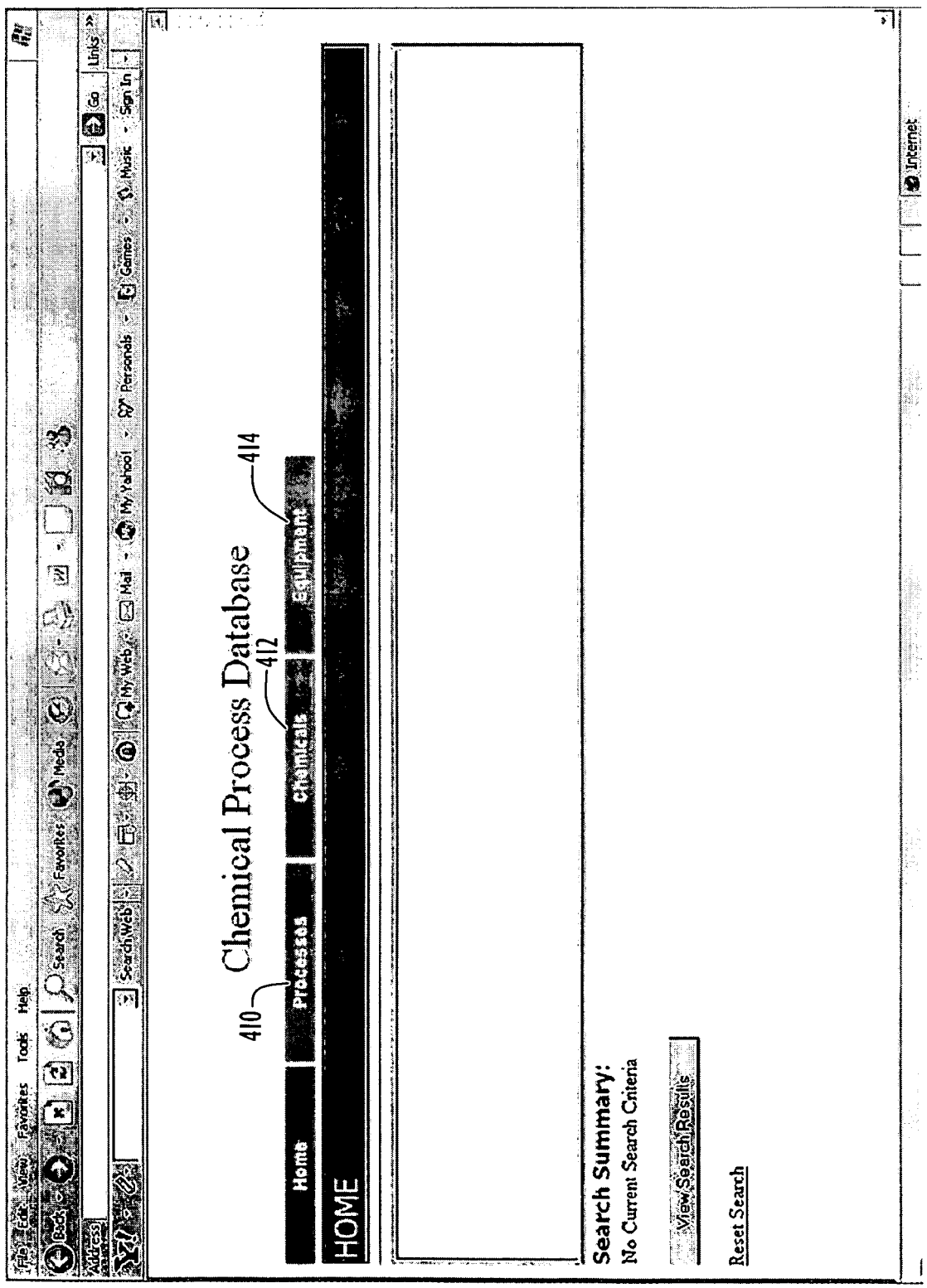
FIG. 6A illustrates an initial screen of a user interface for the system.

Turning to FIG. 5, a first specific example of the chemical database and related characterization analysis method is described in connection with FIGS. 6A, 6B and 7-11 First, in an initial menu page shown in FIG. 6A, there are provided a Processes link 410, a Chemicals link 412 and an Equipment link 414. Selecting one of these links directs the user to the corresponding portion of the database where search terms for Chemicals, Processes or Equipment, respectively, can be added to the search criteria. In this example, the user selects the Chemicals link 412 and is directed to the page shown in FIG. 6B. On this page, the list of all chemicals in the database is shown at reference numeral 420. The user can scroll down this list to select a chemical by name. Alternatively, the user can filter this list down by a particular chemical category as shown at reference numeral 422. In step 310, if a user knows the chemical name of an observed substance he/she can add that chemical to the search criteria by selecting the "Add to Search" link next to that chemical's name. Otherwise, the user can enter in blank field 424 next to "Search For:" a description of the observed properties of a substance whose chemical identity is not known. For example, as shown in FIG. 6, the user may enter the term "brown solid" as an observable to be searched in the chemical comments (same as chemical notes) field of chemicals in the database. Next, in step 320, the user runs a search based on "brown solid" entered as the only chemical related observable. FIG. 7 shows the results of a search run against that observable, and lists several candidate chemicals that have "brown solid" in their chemical notes field.

Figure 8:
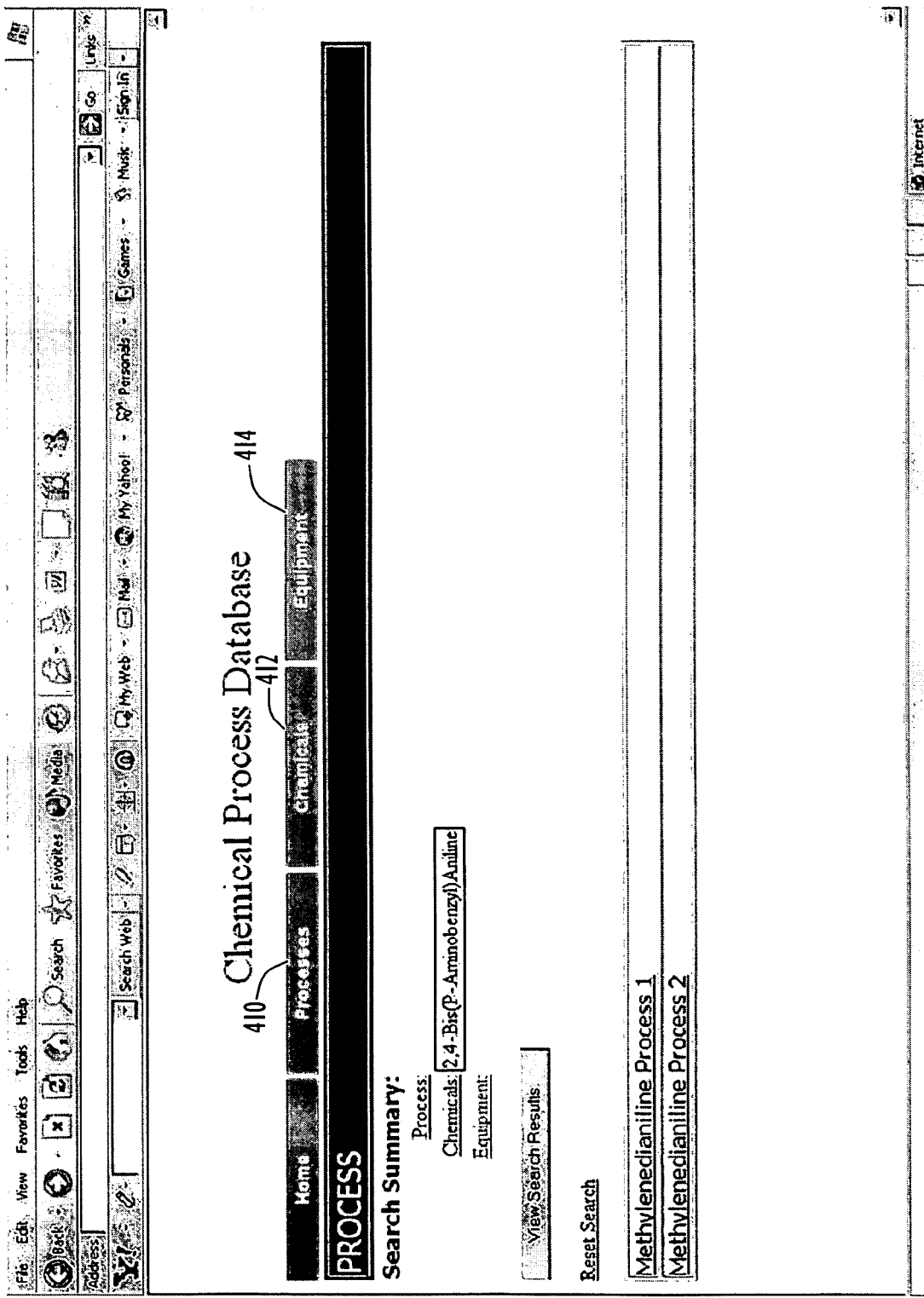

Next, in step 330, the user can select one or more of the candidate chemicals listed in FIG. 7 to further refine the search. For example, the chemical 2,4-Bis(P-Aminobenzl) Aniline is selected by the user clicking on the "Add to Search" link next to that chemical. In so doing, the user has told the system to add that chemical to the search criteria, to be used together with any other observed data entered by the user up to this point in the search, and to run a search with that chemical against the database to return a list of all candidate chemical processes related to 2,4-Bis(P-Aminobenzl)Aniline. This also causes the system to switch to the Process page shown in FIG. 8, showing beneath the "Search Summary" heading that 2,4-Bis(P-Aminobenzl)Aniline has been added to the Chemicals search field for the search criteria. With the candidate chemical selected above, there are two candidate chemical processes returned and displayed at 430: Methylenedianiline Process 1 and Methylenedianiline Process 2.

The user interface for the database may be designed such that the system keeps track of the search criteria as it is modified during a search session, when selecting the Add to Search button for chemicals or equipment to be added to search criteria. For example, the system may keep track of the search criteria in a manner similar to the "shopping cart" function of e-commerce web applications. When the View Search Results button is selected, the system retrieves and displays the list of processes that match the current state of the search criteria.

Figure 9:
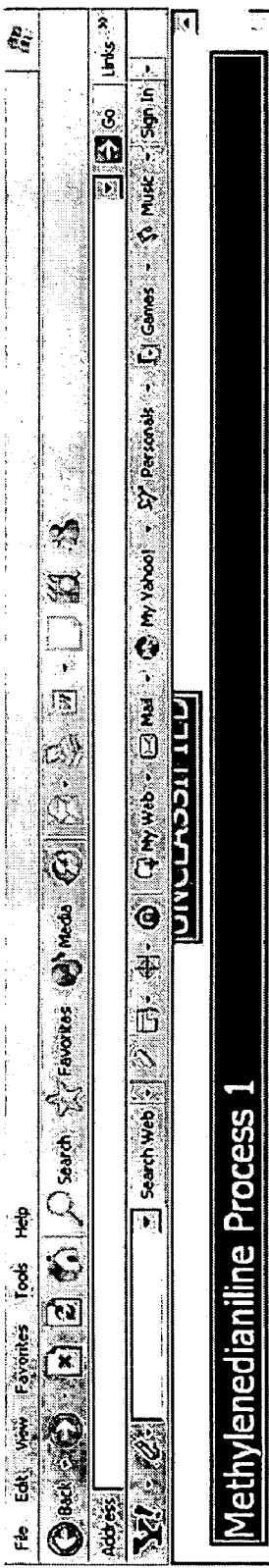
Figure 10:
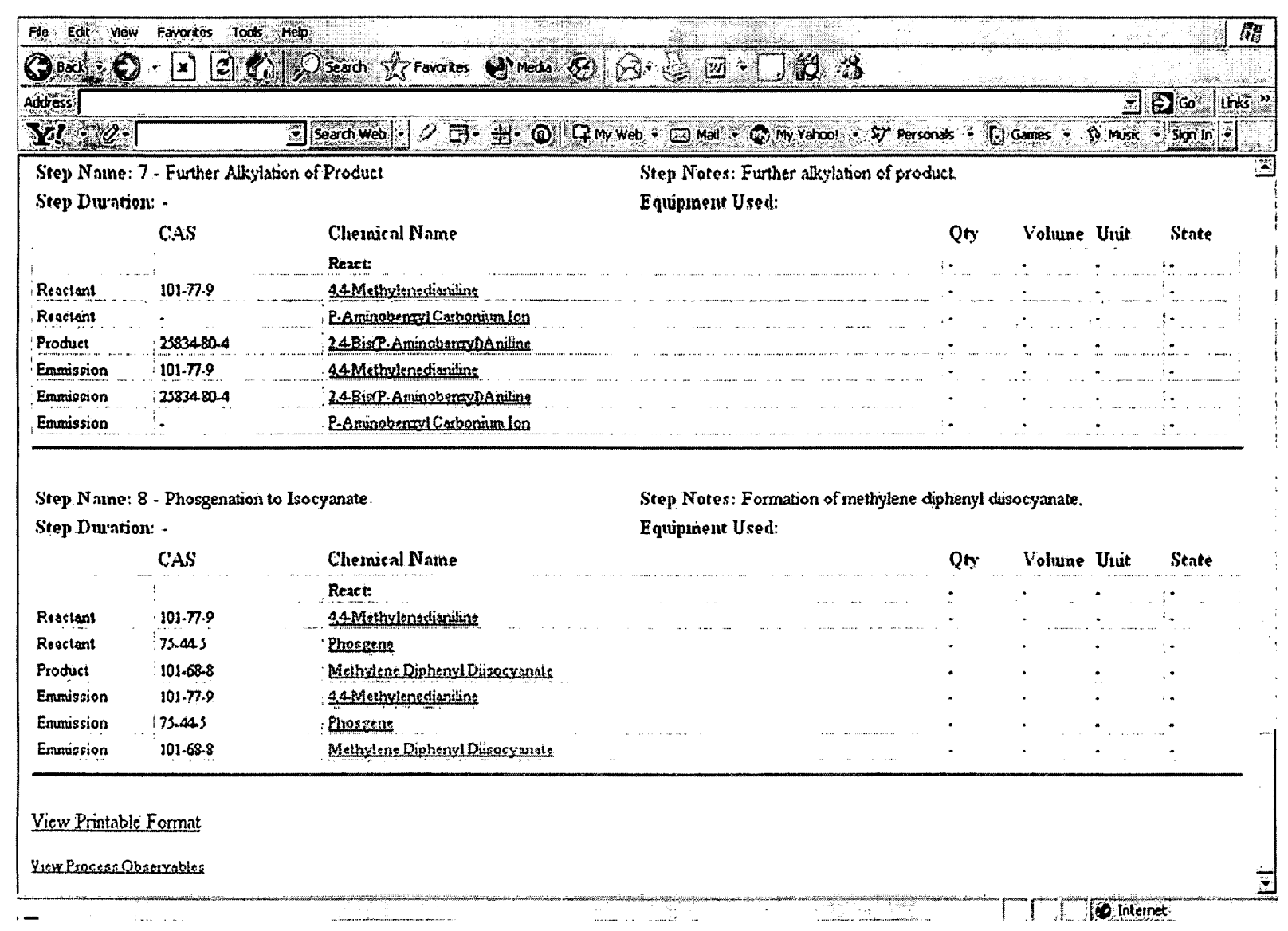
Figure 12:
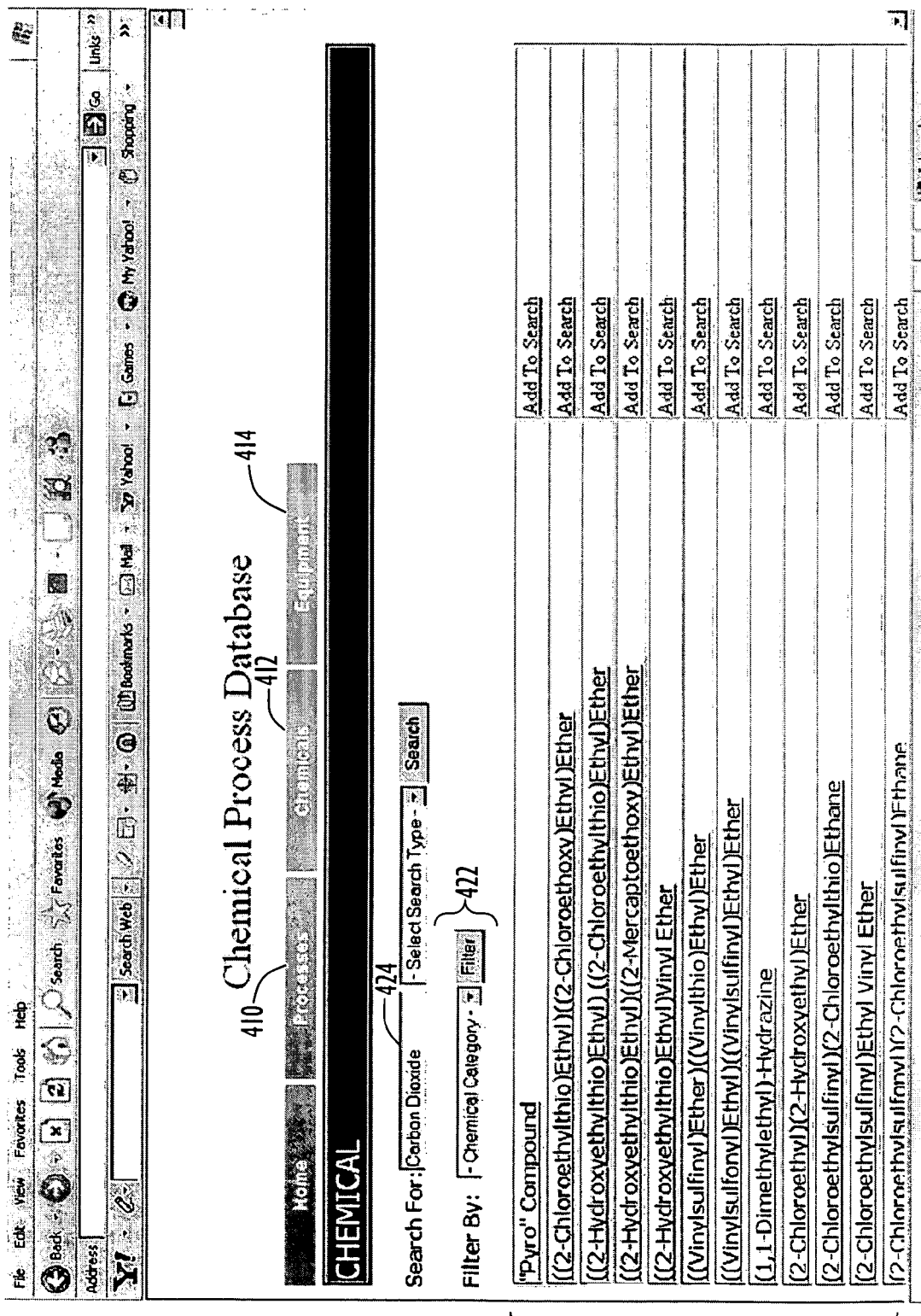

FIGS. 9-11 illustrate the data that is stored in the database and displayed for Methylenedianiline Process 1, as an example. This data is displayed when the user selects that process from the screen shown in FIG. 8. FIG. 9 shows some of the general information for Methylenedianiline Process 1, including its Process Categories, Process Notes and Information Source. Recall that these are fields of the data records in the database explained above in connection with FIG. 3. The first step of this process, Step Name 1—Condensation, is shown together with its Step Notes and Equipment Used. In addition, each of the chemicals involved in the step are listed by name and CAS, as well as each chemical's function (reactant, emission, solvent, etc.). This information is represented in the Step Attribute data records related to this process. In addition, details on any particular chemical in a step may be displayed by selecting the link for that chemical's name. FIG. 10 illustrates data associated with steps 7 and 8 of this process (steps 2-6 are omitted for brevity) and a link at the bottom of the screen called "View Process Observables". When a user selects this link, a list of observables for this process are displayed as shown in FIG. 11. These observables include chemicals and equipment that may be detected, and the associated "use" or function of each chemical and equipment in the process. A user can use the list of observables to go back and perform additional investigations to determine whether these observables are also found, thereby providing additional confirmation that the Methylenedianiline Process 1 is occurring.

Figure 13:
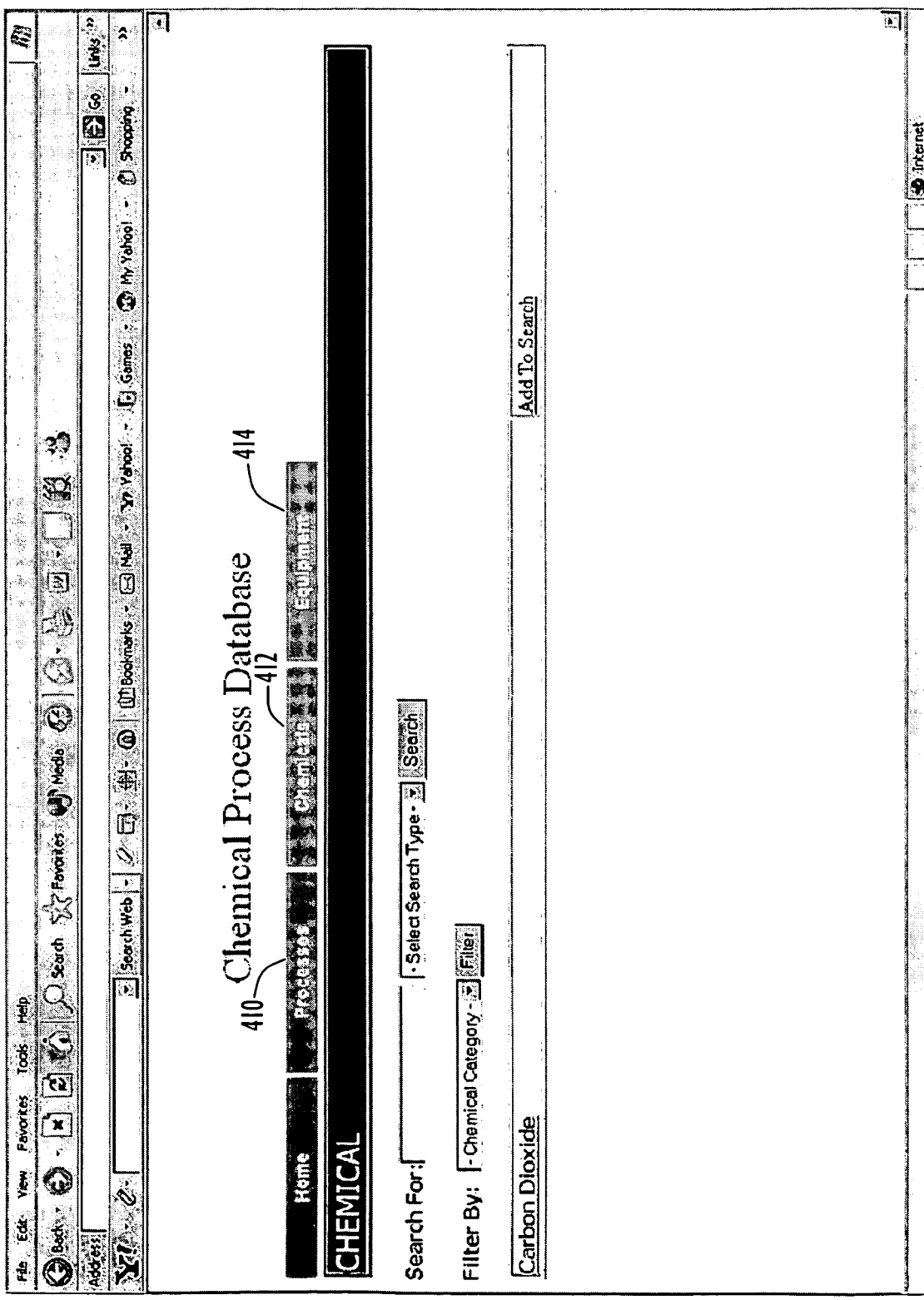
Figure 14:
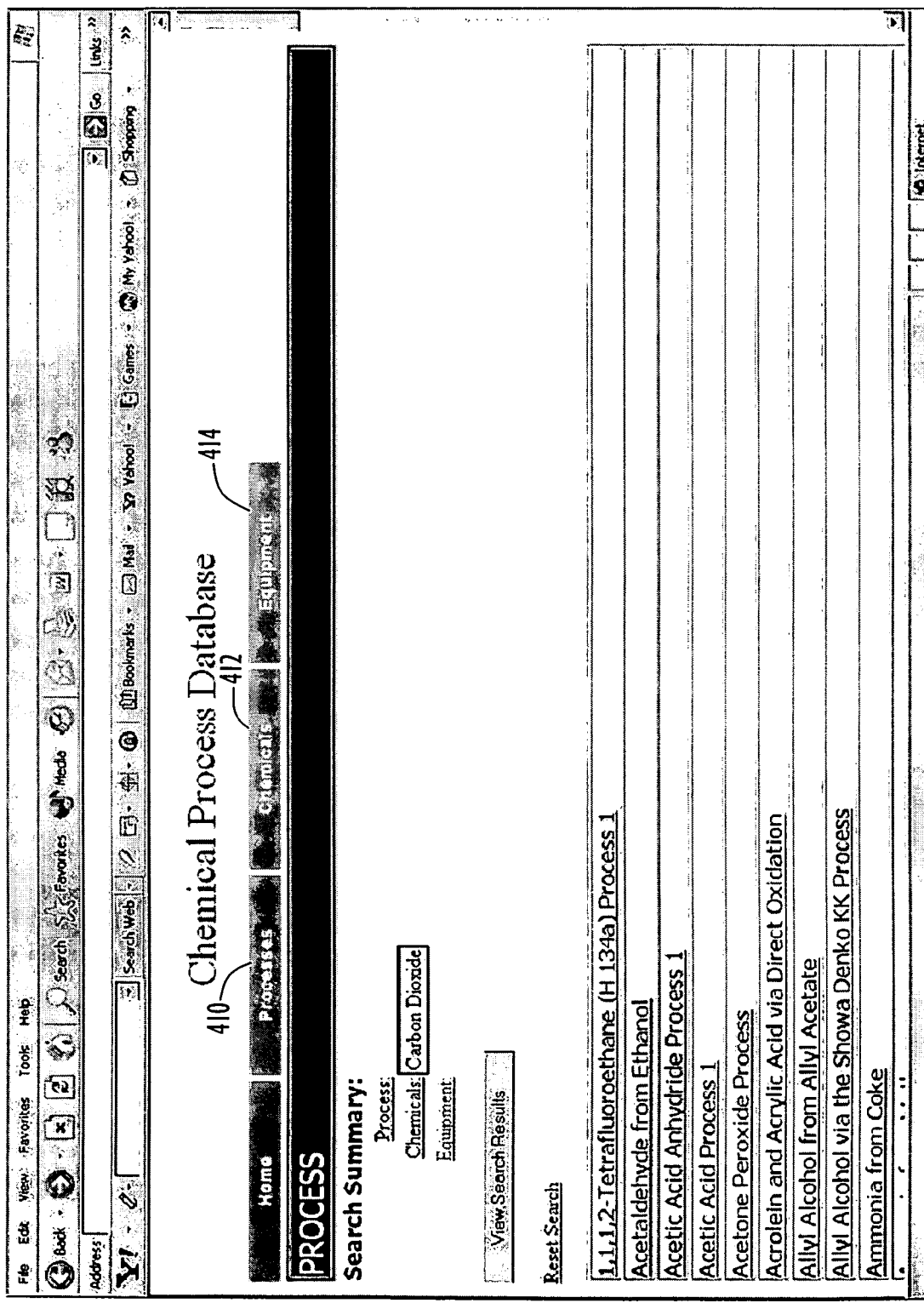
Figure 16:
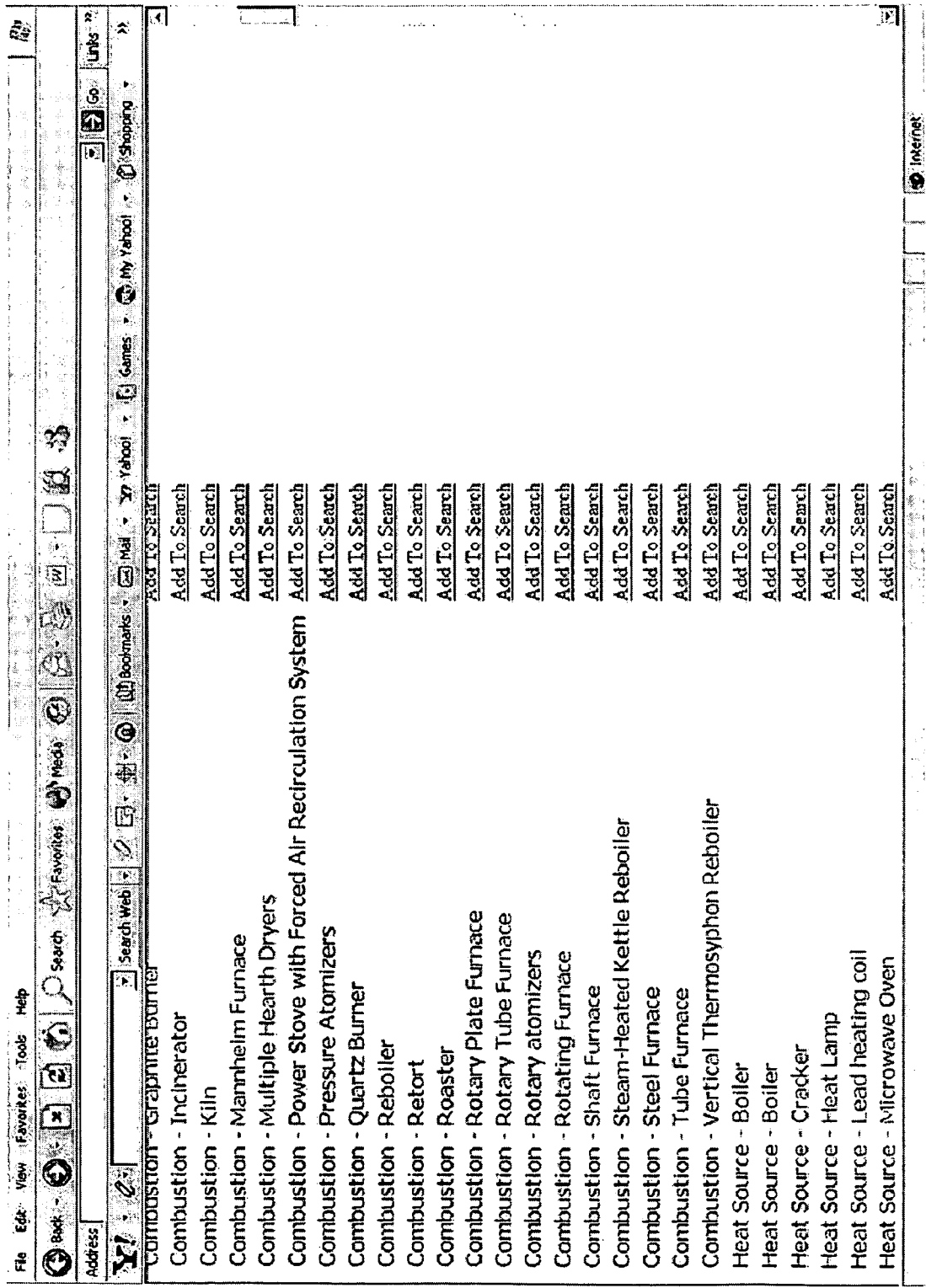

Turning to FIGS. 12-20, with continued reference to FIG. 5, another example of a search will be described. In this example, the search begins by entering Carbon Dioxide as the Chemical to be added to the search criteria. This is carried out in steps 310-330 of the process 300 shown in FIG. 5 on the Chemicals page shown in FIG. 12. If an observed chemical is known by name, it can be entered by scrolling down the list 420, or by entering the chemical name in the blank 424 next to "Search For:". When the Search button is selected on the Chemicals page shown in FIG. 12, the next page displayed is shown in FIG. 13. From this page, the chemical Carbon Dioxide can be added to the search criteria by selecting the Add to Search link. The page displayed in response to making this selection is shown in FIG. 14, where the list 430 is displayed for all the candidate process in which Carbon Dioxide is related. Next, in step 340, additional observables are entered. For example, the user may select the Equipment link 414 to go to the Equipment page shown in FIG. 15. On this page, there is displayed a list 440 of all equipment in the database, organized by categories. If the name of the equipment observed is not known, the user may enter a description of it and command the system to search the database and find the equipment name that matches that description in the Equipment Notes field in step 350. Alternatively, the user may scroll through the list 440 and directly select a particular equipment as shown in FIG. 16, where the user selects the "Add to Search" button for a Tube Furnace, under the category of Combustion equipment. In response to this selection, the system returns the user to the page shown in FIG. 17, where the Search Summary indicates Carbon Dioxide for Chemicals and Tube Furnace for Equipment. In addition, the system runs the search criteria against the database to return a list of candidate processes. In this case, only a single candidate process is returned: Ethylene and Propene from Naptha Cracking.

Figure 17:
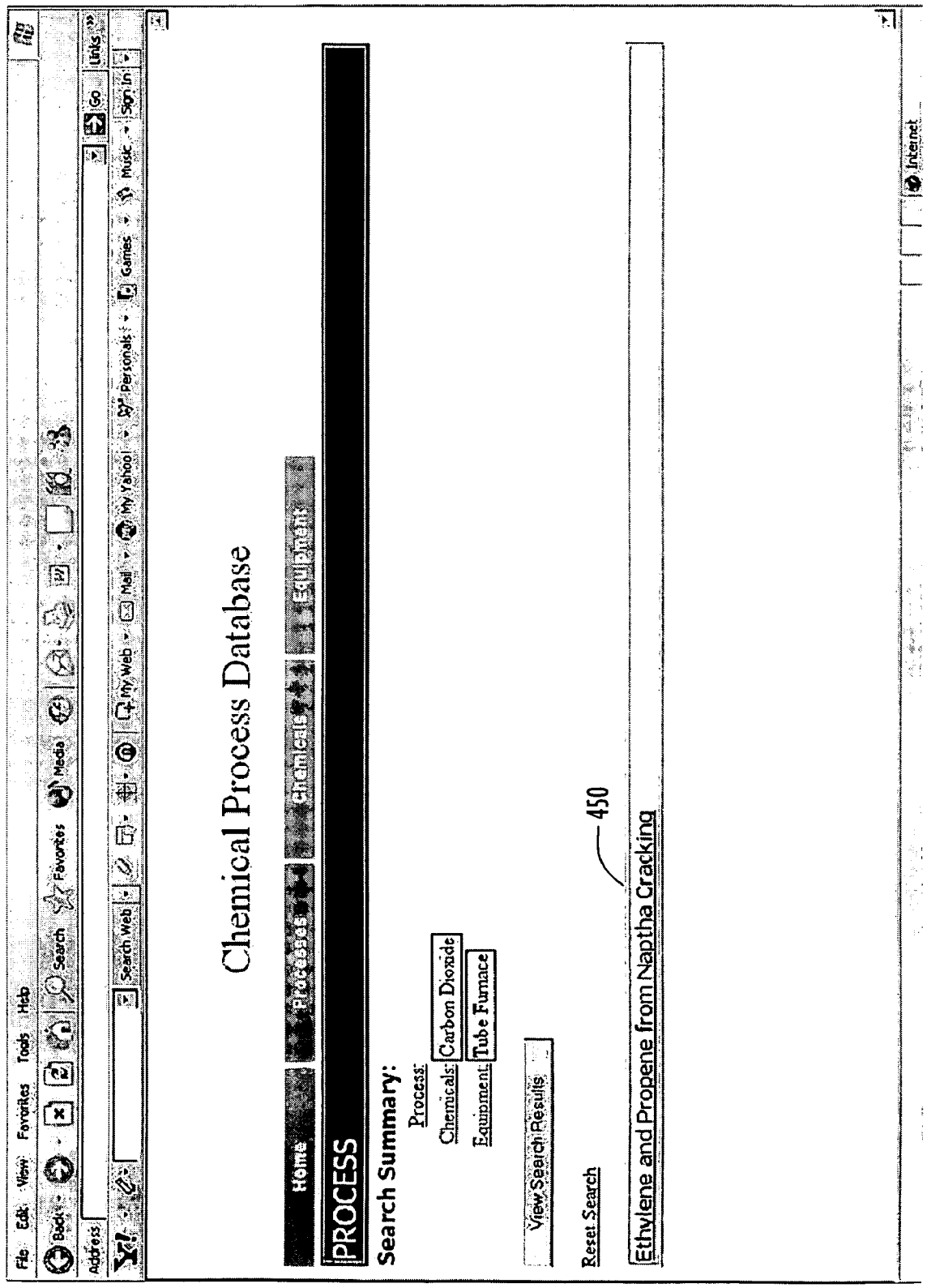
Figure 18:
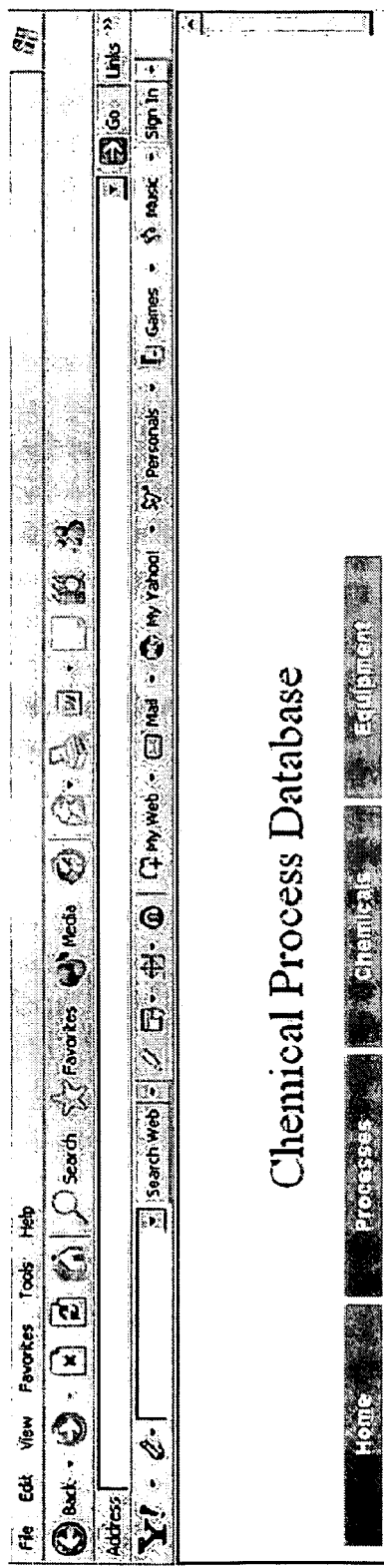

Details about this process can be displayed by clicking on the link for it shown in FIG. 17 at reference numeral 450. FIGS. 18 and 19 illustrate portions of the data in the database for the Ethylene and Propene from Naptha Cracking process. In particular, in FIG. 19, the user may select the link "View Process observables" to view a list of observables, i.e., chemicals that may be detected from the process, and the associated use or function of each chemical in the process. The list of observables for this process is shown in FIG. 20.

When searching the searching criteria against the database, the system may be sensitive to a list of observables A, B and C, so as to return a list of candidate processes that are consistent with observables A, B and C as well as subsets of those observables, e.g., A and B, A and C, and B and C. This is useful in the event that one of the observables (A, B or C) is irrelevant, is a decoy or if there are multiple processes occurring where there originally was thought to be only one process.

The foregoing description is meant by way of example only. For example, other types of data that may be included the database include geographic related information.

Another use of the database system described herein is to select a particular process directly and learn how to make a particular chemical according to that process.

Having described preferred embodiments of new and improved chemical process characterization database system and method, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

The invention claimed is:

1. A computer readable medium storing instructions that, when executed by a computer, cause the computer to:
   a. receive from a user as input observed data derived from observations of a site associated with one or more processes whose identities are not known, wherein the observed data comprises data describing physical characteristics of a substance observed at the site whose role in a process is not limited to a product of a process and data describing physical characteristics or type of equipment observed at the site;
   b. search the observed data against a database that maintains relationships between data for a plurality of processes, data for a plurality of substances, physical characteristics of the substances and the role a substance has in one or more of the plurality of processes and data for a plurality of equipment, physical characteristics of the equipment and the role a piece of equipment has in one or more of the plurality of processes; and
   c. determine an identity of one or more candidate processes among the plurality of processes that are responsible for producing the observed data based on said search.

2. The computer readable medium of claim 1, wherein said instructions that cause the computer to receive comprise instructions for receiving as input the observed data comprising text for one or more of: a name of one or more observed substances, and a name of one or more observed equipment.

3. The computer readable medium of claim 1, wherein said instructions that cause the computer to receive comprise instructions for receiving as input text that describes physical characteristics including one or more of a color, physical state and odor of a substance observed at the site and text that describes the physical characteristics of equipment including one or more of size, color and material of structures observed at the site and text that describes a type of equipment.

4. The computer readable medium of claim 1, wherein said instructions that cause the computer to search comprise instructions for searching said observed data against said database that relates data pertaining to substances and equipment to the processes that use or involve those substances and equipment.

5. The computer readable medium of claim 1, wherein said instructions that cause the computer to search comprise instructions for using as a search term a name of an observed substance for searching against data in the database comprising text for the names of substances involved in each step of a process.

6. The computer readable medium of claim 1, wherein said instructions that cause the computer to search comprise instructions for using as a search term text describing a physical characteristic of an observed substance for searching against data in the database that comprises a textual description of physical characteristics for each of the plurality of substances, to obtain a list of one or more substances that have physical characteristics matching said observed data.

7. The computer readable medium of claim 6, wherein said instructions that cause the computer to search comprise instructions for using as a search term text comprising names of substances for searching against data in the database comprising text for the names of substances involved in each step of a process, to thereby return a list of one or more processes that involve said one or more substances.

8. The computer readable medium of claim 1, wherein said instructions that cause the computer to search comprise instructions for using as a search term text for a name of observed equipment, against data in the database that comprises text for the names of equipment involved in each step of a process.

9. The computer readable medium of claim 1, wherein said instructions that cause the computer to search comprise instructions for using as a search term text describing a physical characteristic of observed equipment for searching against data in the database that comprises, a textual description of the physical characteristics of a plurality of equipment, to obtain a list of equipment having physical characteristics matching the observed data.

10. The computer readable medium of claim 1, wherein said instructions that cause the computer to search comprise instructions for searching one or more subsets of the observed data against the database to determine one or more candidate processes that can create subsets of the observed data.

11. The computer readable medium of claim 1, and further comprising instructions that cause the computer to produce display data for displaying text for a list of one or more candidate processes.

12. The computer readable medium of claim 11, wherein said instructions that cause the computer to produce display data comprise instructions for displaying, for each process in the list, text for one or more of: one or more steps in the candidate process, a list of substances involved in each step, information describing the function of each substance in a step and a list of equipment used in the candidate process.

13. The computer readable medium of claim 12, wherein said instructions that cause the computer to produce display data comprise instructions for displaying, for each candidate process in the list, textual information describing one or more observable substances, equipment or other detectable indications associated with the candidate process to guide further data gathering.

14. The computer readable medium of claim 1, wherein said instructions that cause the computer to receive input comprise instructions to receive observed data pertaining to a substance observed at the site whose role in a process is a catalyst, solvent, reactant, byproduct, product or emission.

15. A method for analyzing data to determine an identity of a chemical process, comprising:
   a. storing data in a database that relates data for a plurality of processes, data for a plurality of substances, physical characteristics of the substances and the role a substance has in one or more of the plurality of processes, and data for a plurality of equipment, physical characteristics of the equipment and the role each piece of equipment has in one or more of the plurality of processes;
   b. searching the database with search criteria comprising observed data derived from observations of a site associated with one or more processes whose identities are not known in order to determine an identity of one or more candidate processes among the plurality of processes that are responsible for producing the observed data, wherein the observed data comprises data describing physical characteristics of a substance observed at the site whose role in a process is not limited to a product of a process and data describing physical characteristics or type of equipment observed at the site; and
   c. presenting to a user data pertaining to said one or more candidate processes.

16. The method of claim 15, wherein storing comprises:
   a. storing process data pertaining to each of a plurality of processes, wherein said process data comprises text for one or more of: a name of the process, a list of one or more steps in the process, a list of substances involved in each step, information describing the function of each substance in a step and a list of equipment used in the process;
   b. storing data for each of a plurality of substances, wherein the data for each substance includes text for at least one of: descriptive data pertaining to physical characteristics of the substance and a name; and
   c. storing equipment data pertaining to each of a plurality of equipment that may be used in any one or more of the processes, wherein said equipment data includes text for at least one of: descriptive data pertaining to physical characteristics of the equipment and an equipment name.

17. The method of claim 16, and further comprising cross referencing data for a substance listed in the process data with data for that substance listed in the substance data, and cross referencing data for equipment listed in the equipment data with data for that equipment listed in the process data.

18. The method of claim 17, and further comprising receiving from a user the observed data comprising text for a name of one or more observed substances, and a name of one or more observed equipment.

19. The method of claim 17, and further comprising receiving the observed data comprising text for a description of physical characteristics including one or more of a color, physical state and odor of a substance observed at the site, and a description of physical characteristics of equipment comprising one or more of size, color and material of structures observed at the site and type of one or more observed equipment.

20. The method of claim 19, and further comprising receiving the observed data comprising text for a name of one or more substances and a name of one or more observed substances.

21. The method of claim 15, wherein searching comprises searching subsets of the observed data against the database to determine one or more candidate processes that can create subsets of the observed data.

22. The method of claim 15, and further comprising displaying, for each candidate process determined to possibly create the observed data, textual information describing one or more other observable substances, equipment or other detectable indications associated with the candidate process to guide further data gathering.

23. The method of claim 15, and further comprising displaying text for a list of the one or more candidate processes possibly occurring as a result of the search based on said observations.

24. The method of claim 15, and further comprising generating the observed data by observing the site without directly monitoring the one or more processes.

25. The method of claim 15, wherein searching comprises searching the database with observed data comprising data pertaining to a substance observed at the site whose role in a process is a catalyst, solvent, reactant, product, byproduct, or emission.

26. A computer readable medium storing instructions that, when executed by a computer, cause the computer to:
   search a database that stores and maintains relationships between, data for a plurality of processes, data for a plurality of substances, physical characteristics of the substances and the role each substance has in one or more of the processes and data for a plurality of equipment, physical characteristics of the equipment and the role each piece of equipment has in one or more of the processes, wherein the search is performed with search criteria comprising observed data derived from observations made by a user of a site associated with one or more processes whose identities are not known in order to determine an identity of the one or more candidate processes among the plurality of processes that are responsible for creating the observed data, wherein the observed data comprises data describing physical characteristics of a substance observed at the site whose role in a process is not limited to a product of a process and data describing physical characteristics or type of equipment observed at the site; and present to a user data pertaining to said one or more candidate processes.

27. The computer readable medium of claim 26, wherein said instructions that cause the computer to receive the observed data from the user comprise instructions for the observed data comprising text for a name of one or more observed substances if a name can be determined, a name of one or more observed equipment if a name can be determined, a description of physical characteristics including one or more of a color, physical state and odor of a substance observed at the site, and a description of physical characteristics of equipment including one or more of size, color and material of structures observed at the site and a type of equipment.

28. The computer readable medium of claim 27, wherein said instructions that cause the computer to search comprise instructions for searching said observed data containing text describing a physical characteristic of an observed substance against data pertaining to a plurality of substances comprising a textual description of physical characteristics for each of the plurality of substances, to obtain a list of one or more substances that have physical characteristics matching said observed data.

29. The computer readable medium of claim 26, wherein said instructions that cause the computer to search comprise instructions for searching said observed data containing a name of an observed substances against process data pertaining to a plurality of processes, wherein said process data comprises text for the names of substances involved in each step of a process.

30. The computer readable medium of claim 26, wherein said instructions that cause the computer to search comprise instructions for searching said observed data containing text describing physical characteristic of observed equipment, and wherein said database comprises a textual description of the physical characteristics of a plurality of equipment, to obtain a list of equipment having physical characteristics matching the observed data.

31. The computer readable medium of claim 30, wherein said instructions that cause the computer to search comprise instructions for searching the database against process data pertaining to a plurality of processes, wherein said process data comprises text for the names of equipment involved in each step of a process, to thereby return a list of one or more candidate processes that involve said equipment.

32. The computer readable medium of claim 26, and further comprising instructions that cause the computer to produce display data for displaying text for a list of one or more candidate processes.

33. The computer readable medium of claim 32, wherein said instructions that cause the computer to produce display data comprise instructions for displaying, for each process in the list, text for one or more of: one or more steps in the candidate process, a list of substances involved in each step, information describing the function of each substance in a step and a list of equipment used in the candidate process.

34. The computer readable medium of claim 33, wherein said instructions that cause the computer to produce display data comprise instructions for displaying, for each candidate process in the list, textual information describing one or more observable substances, equipment or other detectable indications associated with the candidate process to guide further data gathering.

35. The computer readable medium of claim 26, said instructions that cause the computer to search the observed data against the database comprise instructions that cause the computer to search observed data comprising data pertaining to a substance observed whose role in a process is a catalyst, solvent reactant, byproduct, product or emission.

* * * * *